United States Patent
Smith et al.

(10) Patent No.: US 7,056,307 B2
(45) Date of Patent: Jun. 6, 2006

(54) WEIGHT DEPENDENT, AUTOMATIC FILLING DOSAGE SYSTEM AND METHOD OF USING SAME

(76) Inventors: James E. Smith, 619 E. Broadway, Winters, Runnels County, TX (US) 79567; Bobby J. Myers, 1687 CR 173, Winters, Runnels County, TX (US) 79567; D. Steve Williams, 3705 Ebony Hollow Cove, Austin, Travis County, TX (US) 78739

( * ) Notice: Subject to any disclaimer, the term of this patent is extended or adjusted under 35 U.S.C. 154(b) by 196 days.

(21) Appl. No.: 10/452,775

(22) Filed: Jun. 2, 2003

(65) Prior Publication Data
US 2004/0015123 A1    Jan. 22, 2004

Related U.S. Application Data

(63) Continuation-in-part of application No. 09/947,799, filed on Sep. 6, 2001, now abandoned.

(51) Int. Cl.
*A61M 5/00* (2006.01)

(52) U.S. Cl. ............... 604/207; 604/186; 604/218; 604/247; 222/380; 222/386; 222/36; 222/323; 222/41

(58) Field of Classification Search ........... 604/890.1, 604/65, 892.1, 67, 68, 71, 118, 120, 121, 604/123–125, 131, 135, 151, 152, 154, 155, 604/187, 181, 183, 186, 218, 246, 247, 35, 604/207; 128/DIG. 12, DIG. 13; 417/500; 222/31–37, 41, 46, 323, 325–327, 372, 373, 222/384, 386, 390
See application file for complete search history.

(56) References Cited

U.S. PATENT DOCUMENTS

| | | | |
|---|---|---|---|
| 3,303,823 A | 2/1967 | Cohen | 119/51.11 |
| 3,656,478 A | 4/1972 | Swersey | 128/214 |
| 3,727,614 A * | 4/1973 | Kniazuk | |
| 3,827,601 A * | 8/1974 | Magrath et al. | |
| 3,859,996 A * | 1/1975 | Mizzy et al. | |
| 4,059,107 A * | 11/1977 | Iriguchi et al. | |
| 4,081,044 A | 3/1978 | Allen | 177/103 |
| 4,266,541 A * | 5/1981 | Landau | |
| 4,280,494 A | 7/1981 | Cosgrove, Jr. et al. | 128/213 |
| 4,308,866 A | 1/1982 | Jelliffe et al. | 128/214 |
| 4,564,360 A * | 1/1986 | Young et al. | |
| 4,589,372 A | 5/1986 | Smith | 119/51 |
| 4,592,742 A * | 6/1986 | Landau | |
| 4,617,876 A | 10/1986 | Hayes | 119/155 |
| 4,733,971 A | 3/1988 | Pratt | 366/141 |

(Continued)

OTHER PUBLICATIONS

*International Search Report*, PCT/US02/04934, Aug. 20, 2002, 2 pp.

(Continued)

Primary Examiner—Cris Rodriguez
(74) Attorney, Agent, or Firm—Patent & Trademark Services, Inc.; Joseph H. McGlynn

(57) ABSTRACT

The invention concerns a syringe for administering medication to an animal. The syringe includes a handle that may be manually actuated to dispense medication to the animal. The syringe also includes a valve that controls the flow of medication both into and out of the syringe. A sensor device on the syringe monitors when the medication has been administered in order to inform any attached pump that the syringe may be refilled. An LED informs the user when the syringe has been filled with medication and is ready for the administration of medication to the animal.

7 Claims, 15 Drawing Sheets

U.S. PATENT DOCUMENTS

| | | | |
|---|---|---|---|
| 4,804,110 A * | 2/1989 | Sperry et al. | |
| 4,887,554 A | 12/1989 | Whitford | 119/159 |
| 4,941,809 A | 7/1990 | Pinkerton | 417/500 |
| 5,015,157 A | 5/1991 | Pinkerton et al. | 417/500 |
| 5,020,980 A | 6/1991 | Pinkerton | 417/500 |
| 5,044,889 A | 9/1991 | Pinkerton | 417/53 |
| 5,246,354 A | 9/1993 | Pardinas | 417/500 |
| 5,254,092 A * | 10/1993 | Polyak | |
| 5,279,210 A | 1/1994 | Pinkerton | 92/170.1 |
| 5,315,505 A | 5/1994 | Pratt et al. | 364/413.01 |
| 5,322,511 A | 6/1994 | Armbruster et al. | 604/155 |
| 5,560,317 A | 10/1996 | Bunyan et al. | 119/174 |
| 5,778,893 A | 7/1998 | Potter | 128/898 |
| 5,803,906 A | 9/1998 | Pratt et al. | 600/300 |
| 5,807,340 A * | 9/1998 | Pokras | |
| 5,865,811 A * | 2/1999 | Doying, Sr. et al. | |
| 5,951,516 A | 9/1999 | Bunyan | 604/143 |
| 5,968,017 A * | 10/1999 | Lampropoulos et al. | |
| 6,000,361 A | 12/1999 | Pratt | 119/51.02 |
| 6,099,502 A | 8/2000 | Duchon et al. | 604/131 |
| 6,367,664 B1 * | 4/2002 | Bunyan et al. | |
| 2002/0123716 A1 * | 9/2002 | VanDiver et al. | |
| 2005/0020983 A1 * | 1/2005 | Schreijag et al. | |
| 2005/0085767 A1 * | 4/2005 | Menassa | |

OTHER PUBLICATIONS

Micro Beef Technologies; "Auto-Doser™ Weight Adjusted Dosing System," brochure, 2 pages; undated.

Micro Beef Technologies; "Drug-Trac® Animal Health System," brochure; 2 pages; undated.

Syrvet, Inc., "Top Line Pour-On Applicator," product sheet; 1 page.

Fluid Metering, Inc., "Dispensers & Metering Pumps," brochure, Copyright 1998, 6 pages.

Fluid Meeting, Inc., "Valveless Dispensers & Metering Pumps 2000," Catalog, Copyright 2000, 30 pages.

Lextron, Inc., "VetRecords™". VetRecord System manual, undated.

* cited by examiner

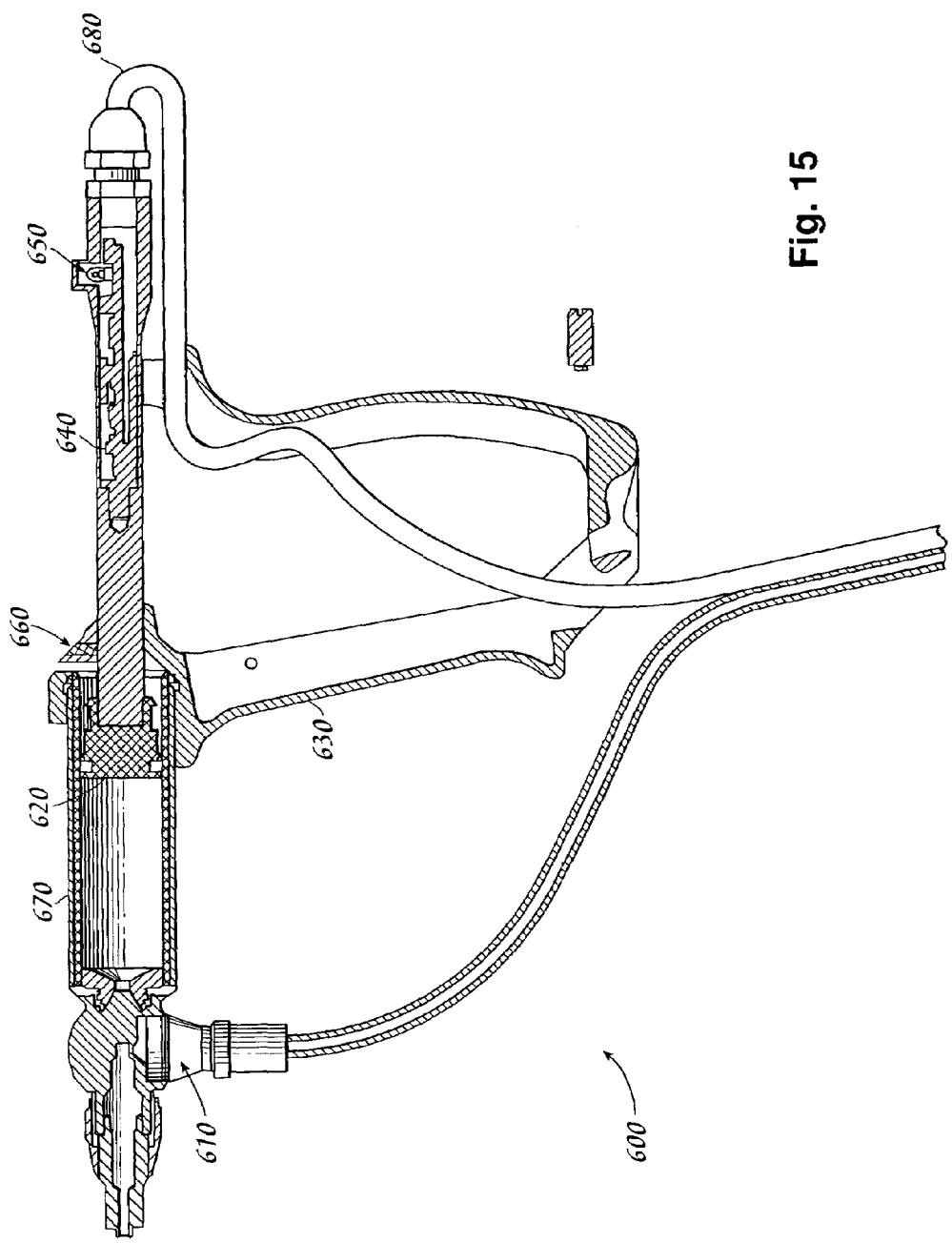

WEIGHT DEPENDENT, AUTOMATIC FILLING DOSAGE SYSTEM AND METHOD OF USING SAME

CROSS-REFERENCE TO RELATED APPLICATION

The present application is a continuation-in-part of Application Ser. No. 09/947,799, filed on Sep. 6, 2001 now abandoned.

TECHNICAL FIELD

The present invention relates generally to a system and method adapted to dispense various amounts of various substances to a variety of subjects, and more particularly relates to a system and method adapted to dispense various dosages of various medications to a variety of subjects, typically animals.

BACKGROUND INFORMATION

It is often desirable to treat large numbers of individuals or animals, referred to herein generally as subjects, with a substance, such as a medication or other material, with speed, efficiency, accuracy, and accurate maintenance of records. Often, the amount of the substance to be administered to the subject is based upon the weight of the subject. Generally, this requires weighing the subject and then calculating the amount of the substance based upon the subject's weight. After calculating the required amount, a delivery device, such as a syringe, is filled with the proper amount of the substance to be administered. Such a procedure can be time intensive, particularly when the number of subjects to be treated is great and the weight of the subjects vary.

As an example, the livestock industry requires routine vaccinating, medicating and/or treating of cattle or livestock. There are many diseases and illnesses contracted by livestock that need to be treated with various drugs and medications. Failure to properly treat the animals can result in significant losses to the rancher or feedlot or other party responsible for the livestock. Typically, the livestock is segregated into groups according to general size and weight. Often, the weight variation in a group of subjects is plus or minus 25% of the average weight of the group. Typically, the same amount of medication is administered to each of the subjects within a particular group. As a result, certain of the livestock are under-medicated while certain of the others are over-medicated. In both of these cases, unnecessary expense is incurred. In the case of the over-medicated livestock, the additional cost is from the unneeded, excessive amount of medication being administered while at the same time increasing tissue residue thereby increasing time until slaughter. In the case of the under-medicated livestock, the additional cost results from having to re-medicate the animal additional times, loss in performance, and significantly increased mortality. Furthermore, a decrease in market price is incurred for meat that cannot be sold as "grade" quality because the animal has a history of illness. These under-medication related problems result in an added expense per animal.

The size of the problem in the cattle feeding industry is substantial. In the United States alone, over 23.5 million head of cattle passed through the nation's feedlots in 1999. It is estimated that feedlots have a "sick rate" of approximately 25–30%. It is a common cow/calf procedure to wean and market calves simultaneously. Therefore, calves go from the farm or ranch to an order buyer's pens or an auction barn before ending up at the feedlot. Any livestock holding facility is a "cesspool" for pathogens that affect young cattle. Many of these calves have had only minimal, or sometimes no, vaccinations at home so they are serologically naive. Some of the calves have not received proper nutrition prior to weaning, resulting in immune incompetency. The added stress of weaning, hauling, and being "marketed" while at the same time being exposed to massive doses of pathogenic organisms can lead to resultant sickness and possible death loss. A large percentage of calves fall ill while moving through the feedlot process.

Both bacterial and viral pathogens are involved in feedlot diseases and are manifest as lameness, enteritis, and Bovine Respiratory Disease (BRD). The viral pathogens IBR, BVD types I and II, PI3, and BRSV, along with the bacterial pathogens *Pasteurella haemolitica, Pasteurella multocida, Haemophilus somnus,* and *Corynebacterium* spp., all play a part in BRD. *Mycoplasma* species can cause pneumonia and arthritis. By far, the greatest losses in life and production are from respiratory disease.

It is common upon arrival at the processing station for cattle to be vaccinated for viral respiratory disease (IBR, BVD, PI3, BRSV) and blackleg (7-way *clostridium*), implanted with a growth stimulant, and treated for internal and external parasites. In high stress situations, antibiotics are sometimes administered simultaneously with vaccinations. The signs of clinical BRD can range from just being off feed with no actual clinical signs to moribundity. Weakness and depression may be hardly noticeable at first. What starts out as rapid, shallow respiration soon becomes labored, open-mouth breathing. As the calf's condition worsens, so do the signs. Ocular and nasal discharges are usually present. Early intervention with appropriate therapy in this disease process is essential in controlling BRD. Processing and treating sick calves is a labor intensive and costly procedure with some antibiotics costing up to $1.00 per cubic centimeter (cc). Treating with the correct dosage for the exact weight is considered necessary. A system including a syringe that could be automatically filled with the appropriate antibiotic, in the correct volume as determined by weight, would save time, drugs, money, and lives.

U.S. Pat. No. 4,589,372 to Smith discloses a dispensing system for supplying and administering a metered dose of a material to a subject based upon the weight of the subject. The delivery system includes a scale for determining the weight of the subject and for generating a weight control signal to a microcomputer. An input keyboard is provided for enabling an operator to select various system initialization data and operating parameters. The microcomputer is responsive to the weight control signal and the weight conversion factor for generating a delivery control signal. A delivery unit is connected to a supply of the material and is responsive to the delivery control signal for supplying a predetermined amount of the material to the subject. The predetermined amount represents an amount which is a function of the weight of the subject and of the weight conversion factor. However, a problem exists in that the delivery of material is indescriminately automated. For example, if the predetermined amount of material to be delivered is 10 cc, the delivery unit will administer all 10 cc at one time. This is problematic because the user may not stop administering the material at 5 cc, reposition the hypodermic needle, and then administer the remaining 5 cc. Administering too much medication to one area of tissue could contaminate muscle tissue. Further, the injection process often requires quite a bit of "feel", which comes from experience, as to which tissue layer the medicament is being administered. If the operator "feels" the needle point is not in the proper tissue layer, he may wish to stop the injection process and re-position the needle. This is not possible with syringes that are completely automated, such as the one disclosed in Smith. Additionally, some medicaments are lethal to humans, especially in the large dosage amounts administered to animals, e.g., 10 cc. An automated syringe, such as disclosed in Smith, is problematic in that an accidental injection into one of the operators would be potentially lethal.

It is desirable to have an automatic dosing syringe system that is highly accurate and dependable. It is also desirable that the automatic filling dosage system be capable of dispensing a variety of substances and be capable of operating in a wide range of ambient temperatures. It is desirable to have a dosage system with a syringe adapted to be automatically filled with the proper amount. It is also desirable to have an automatic filling dosage system and method capable of retrieving and updating the records for the subjects being treated. It is further desirable to have a dosage system that can be easily emptied, cleaned and disinfected without wastage of the medications. It is also desirable to have a manually operated syringe implemented with such a system.

BRIEF DESCRIPTION OF THE DRAWINGS

The objects, advantages and features of the invention will become more apparent by reference to the drawings which are appended hereto and wherein like numerals indicate like parts and wherein illustrated embodiments of the invention are shown, in which:

FIG. 15 is a side elevational view in partial section of another embodiment of a syringe;

DETAILED DESCRIPTION OF THE DRAWINGS

It is to be understood that while the present invention is described below with respect to being used to administer an exact dosage of a substance to a subject such as an animal, the present invention is not limited to this type of application. The present invention may also be used in other applications, including administering shots to humans.

Figure 1:
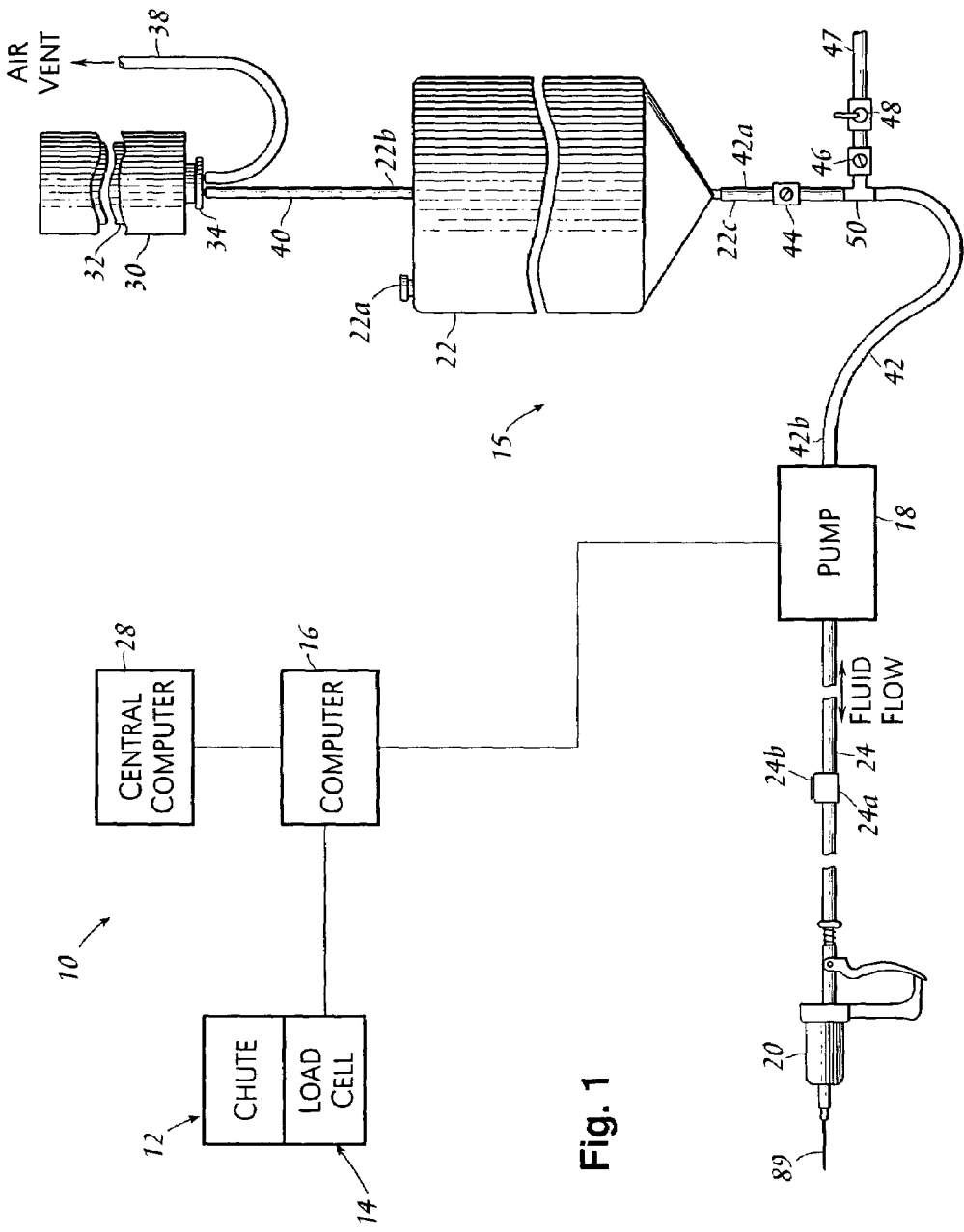
FIG. 1 is a diagrammatic sketch of a weight dependent, automatic filling dosage system according to an embodiment of the present invention showing one unit of the system.

Referring to FIG. 1, the dosage system in one embodiment of the present invention, generally referred to as 10, includes the arrangement and combination of several separate components. The dosage system 10 is used in conjunction with a restraining device 12 and a weighing device 14 as shown in FIG. 1. The restraining device 12 may be a squeeze chute used to secure the animal, and the weighing device 14 may be an electrically-operated load cell used to weigh the animal. Both the squeeze chute 12 and the load cell 14 are commercially available devices and are well known in the industry. The load cell 14 may include a digital output which is transmitted to and read by a system microprocessor-based control device or computer 16. It is to be understood that the output of the load cell 14 could also be an analog output.

With reference to FIG. 1, the dosage system 10 includes a plurality of units 15, with each unit 15 including a pump 18, syringe 20 and reservoir 22. Each unit pump 18 is in fluid communication with the unit reservoir 22 and the unit syringe 20. The syringe 20 is directly connected to the pump 18 via a first connecting tube 24. The pump 18 is connected to the reservoir 22 via a second connecting tube 42. Each sub-combination assembly of pump 18, syringe 20, reservoir 22, and first and second connecting tubes 24 and 42 generally comprises the unit 15. The number of units 15 in the automatic filling dosage system 10 may be determined by how many substances, drugs or chemicals are desired to be available for administering, i.e. one unit for each substance, drug or chemical. For example, a dosage system 10 may include just a single unit, although it is anticipated that a plurality of units, such as 4 to 8, may be more commonly desired.

In addition to the computer 16 receiving weight information on the animal from the load cell 14, the computer 16 receives health-related information on the animal from a central computer 28. The animal's health-related information is provided to the computer 16 to assist in activating the appropriate system units 15 which ultimately leads to filling the appropriate syringe(s) 20 with the appropriate antibiotic/chemical at the correct drug dosage.

Figure 2:
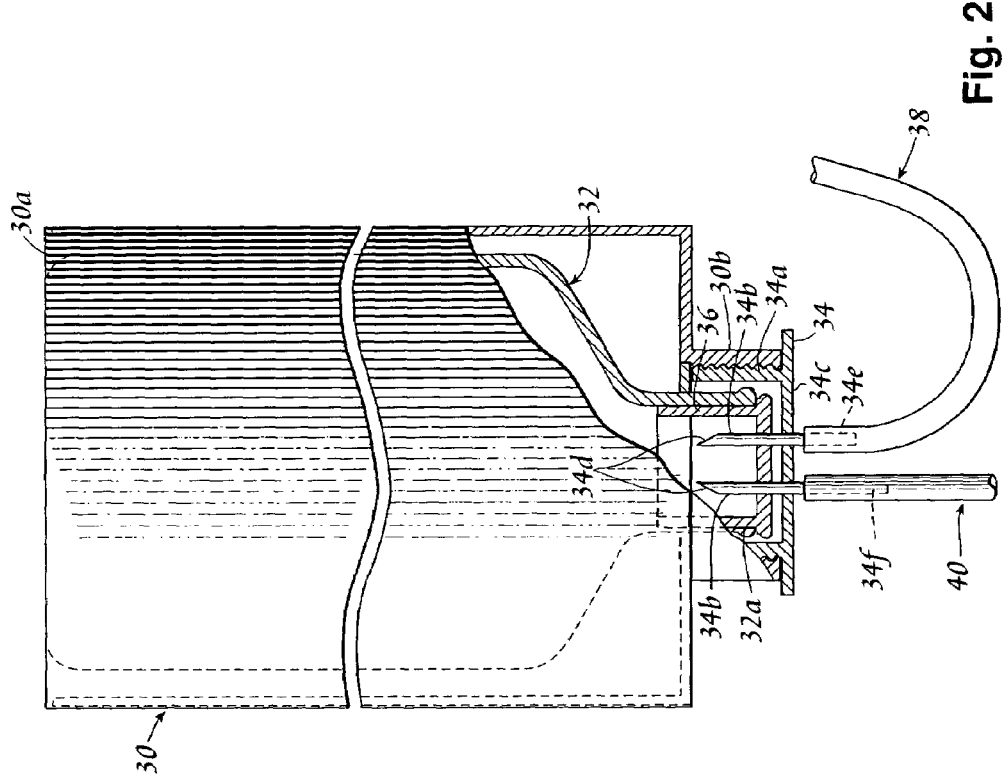
FIG. 2 is an elevational view of a fluid container and filler valve shown in FIG. 1.

Referring to FIGS. 1 and 2, each unit 15 of the dosage system 10 includes a fluid container receptacle 30 for receiving a fluid container 32 containing the drug or chemical. The fluid container receptacle 30 may be a metal container having a large open upper end 30a and a lower, internally threaded neck portion 30b. A container holder 34 having a threaded portion 34a is adapted to engage the neck portion 30b. The container holder 34 includes a pair of tubular spikes 34b extending through a holder plate 34c. The container holder 34 may be made of stainless steel. As shown in FIG. 2, the spikes 34b may have a pointed end 34d for reasons which will be explained below.

Referring to FIG. 2, the fluid container 32 includes a plug 36 in a fluid container opening 32a. The plug 36 is adapted to be punctured by the container holder spikes 34b. The plug 36 forms a fluid-tight seal with the outer surface of the spikes 34b to prevent loss of fluid after being punctured. One spike lower end 34e is connected to an air vent hose 38 and the other spike lower end 34f is connected to the fluid reservoir 22 with a filler hose 40 as shown in FIG. 1.

Figure 3:
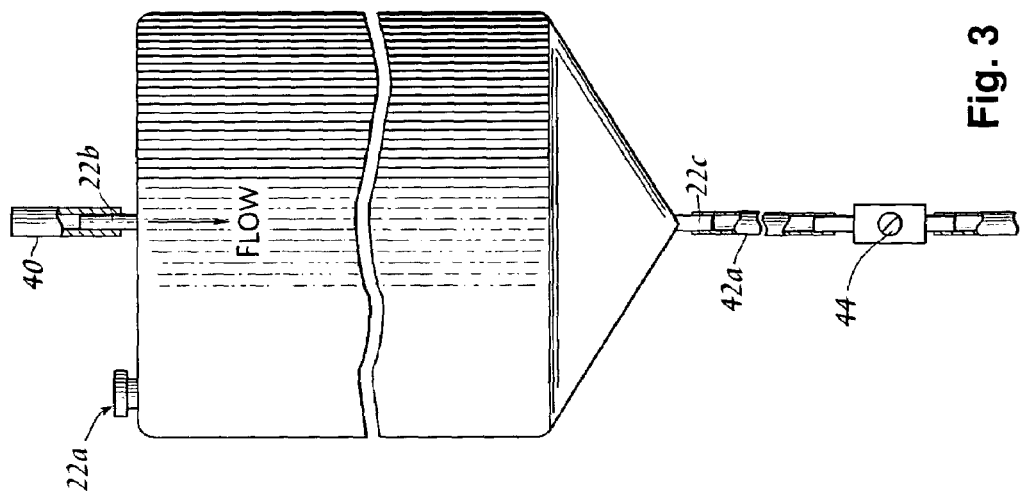
FIG. 3 is an elevational view of a fluid reservoir shown in FIG. 1.

Referring to FIGS. 1 and 3, the fluid reservoir 22 includes an air vent 22a, as for example a flip top filtered air vent with cap. The fluid reservoir 22 has an upper inlet 22b and a lower outlet 22c. The fluid reservoir 22 may have a minimum capacity of 60 milliliters. The second connecting tube 42 is connected at one end 42a to the reservoir outlet 22c and at a second end 42b to the pump 18 as shown in FIG. 1. A first valve 44 is inserted in the second connecting tube 42 between the reservoir 22 and the pump 18 as shown in FIG. 1. The first valve 44 is a two-way stopcock valve. A second valve 46 and a flush port stopcock valve 48 are inserted in a flush line 47 that is branch connected to the second connecting tube 42 for reasons which will be explained below. The second valve 46 is a one-way valve to prevent backflow and contamination.

The system unit pump 18 is a valveless, substantially viscosity-independent pump. The pump 18 used in the system 10 is manufactured by Fluid Metering, Inc. ("FMI") of Syosset, N.Y., Models STH and STQ. To the extent necessary to understand the features and construction of the pump 18 manufactured by FMI, Applicant hereby incorporates by reference U.S. Pat. Nos. 5,279,210; 5,246,354; 5,044,889; 5,020,980; 5,015,157; and 4,941,809.

The pump 18 provides many advantages over diaphragm pumps. The advantages include efficiency, accuracy and ease of maintenance. The FMI pump 18 utilizes one moving part to accomplish both the pumping and valving functions, without valves. In contrast to diaphragm pumps, the internal check valves of a diaphragm pump require continued maintenance. The check valves will eventually clog, leak, and fail over time. Even a minimal decrease in valve efficiency will have an effect on accuracy. The efficiency of these valves will especially be affected at lower temperatures when the product becomes more viscous. The diaphragm pump head is also difficult to heat trace. The pump 18 utilizes sapphire-hard ceramic internals which are dimensionally stable, substantially chemically inert, and will not change shape or dimension over time which provides long term, drift-free accuracy. Diaphragm pumps, on the other hand, use an elastomer for the internal diaphragm which, through constant flexing, changes shape and weakens over time, thus affecting accuracy. The diaphragm is also a maintenance item.

Furthermore, the pump 18 may incorporate a chemically inert ceramic piston instead of, for example, a diaphragm made from elastomers. Consequently, the pump 18 avoids adverse reactions with medications it contacts.

Another advantage provided by the pump 18 is its reversibility. The pump 18 can be reversed by reversing the direction of the motor. The flow direction of the diaphragm pump is completely reliant on the arrangement of the check valves. Therefore, flow direction is fixed and it would be impossible to reverse the pump at the end of the day to recover residual fluid as explained below.

Additionally, the pump 18 has advantages over peristaltic pumps. With respect to accuracy, peristaltic pumps utilize flexible tubing which "loses memory" over time resulting in a continued decrease in accuracy. With respect to maintenance, the pumps 18 require virtually no maintenance while peristaltic tubing must be continually replaced or there will be a significant loss of accuracy, or tubing breakage resulting in loss of product.

Another big advantage provided by the pump 18 is that it is substantially pressure, temperature and viscosity independent due, in part, to its incorporation of sapphire-hard ceramic internals which are dimensionally stable. Peristaltic pumps are designed for low viscosity fluids pumped at low pressures at room temperature. It would be impractical to heat trace peristaltic tubing since it needs to be continually replaced, and the tubing section in direct contact with the pump could not have any heat tracing present. Variations in temperature, pressure, and viscosity will have a direct affect on pump performance and accuracy. Additionally, the peristaltic pump will have difficulty self-priming at colder temperatures because the tubing will become more rigid and lose its sealing characteristics.

Referring to FIG. 1, the first connecting tube 24 includes a check valve 24a and an air vent 24b, as for example a flip top filtered air vent with cap, at the junction of the first connecting tube 24 and the syringe 20.

Figure 4:
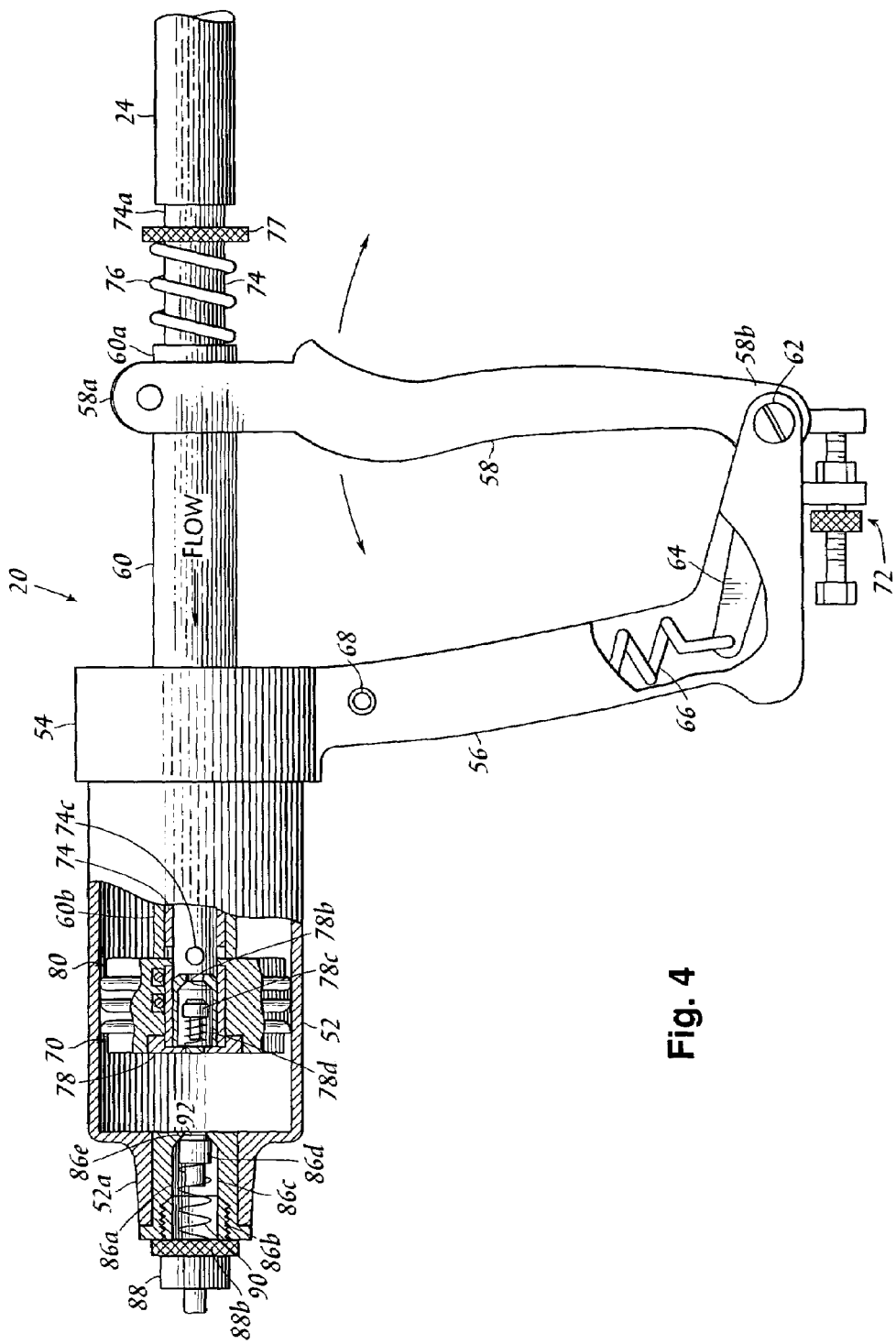
FIG. 4 is a side elevational view in partial section of a fluid retrievable automatic syringe shown in FIG. 1, the syringe shown in the filling process.
Figure 5:
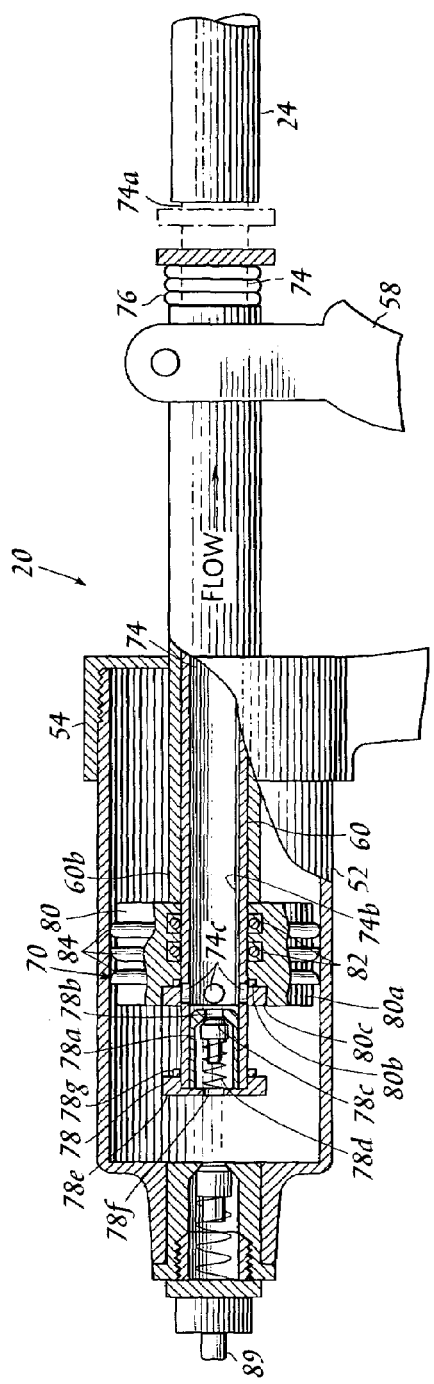
FIG. 5 is a partial side elevational view of the syringe of FIG. 4 shown in the fluid retrieval process.

The syringe 20, as shown in FIGS. 1, 4 and 5, will now be described in detail. The syringe 20 includes a barrel 52, graduated and made of plastic. The barrel 52 connects to an applicator gun body 54, via a threaded connection as shown in FIG. 5. The applicator gun body 54 includes a stationary handle 56 and a compression handle 58. An upper end 58a of the compression handle 58 is connected to a first end portion 60a of a shaft 60, e.g., a hollow shaft. A second end portion 60b of the shaft 60 is connected to a plunger assembly 70. A lower end 58b of the compression handle 58 is pivotally connected to the stationary handle 56 via a pin 62, as shown in FIG. 4.

Although not necessary, it may be desirable to provide a slight spring bias for the compression handle 58. The spring bias may be desirable to aid the filling process of the syringe 20 as will be explained below. One method of accomplishing the spring bias of compression handle 58 is shown in FIG. 4. The lower end 58b of the compression handle 58 includes a leg 64 rigidly affixed to the compression handle 58. The leg 64 is generally perpendicular to the compression handle 58. A spring 66 is connected between the leg 64 and a pin 68 located in the upper portion of the stationary handle 56. When the plunger assembly 70 is in the "closed" or "forward" position at the discharge end of the barrel 52, the spring 66 will exert a slight force on the compression handle 58 (in a clockwise direction as shown in FIG. 4) to provide some assistance in forcing the plunger assembly 70 rearwardly (to the right) as fluid enters the barrel 52.

Referring to FIG. 4, an optional adjustable stop assembly 72 is shown which can be used to limit the clockwise rotation of the compression handle 58 and the rearward movement of the plunger assembly 70. The feature of the adjustable stop assembly 72 is well known to those skilled in the art.

Still referring to FIG. 4, an inner tubing 74, e.g., rigid tubing, extends through the hollow shaft 60. A rear end 74a of the inner tubing 74 is connected to the first connecting tube 24. It is to be understood that the fluid is delivered by the first connecting tube 24 to the inner tubing 74. A compression spring 76 fits onto the inner tubing 74 at a location between the compression handle 58 and a stop ring 77 attached to the inner tubing 74. The compression spring 76 maintains tension on the inner tubing 74 for reasons which will be explained below. A forward end 74b of the inner tubing 74 extends to the plunger assembly 70.

Referring to FIG. 5, the plunger assembly 70 is shown as comprising an inner plunger assembly 78 and an outer plunger assembly 80. The outer plunger assembly 80 includes a plunger body 80a having a bore 80b extending therethrough. The plunger body 80a, cylindrical in shape, is attached to the second end portion 60b of the hollow shaft 60. At least one inner tubing seal 82 is received in the body bore 80b to form a fluid seal between the plunger body 80a and the inner tubing 74. The plunger body 80a receives one or more circumferential seals 84 on its cylindrical outer surface to form a fluid seal between the plunger body 80a and the barrel 52.

Still referring to FIG. 5, the inner plunger assembly 78 is installed in the forward end 74b of the inner tubing 74. The inner plunger assembly 78 includes a valve seat member 78a received in the inner tubing 74. The valve seat member 78a has a seat 78b adapted to seal with a valve body 78c. The valve body 78c is spring biased against the seat 78b via a spring 78d. A cap member 78e having a bore 78f therethrough is attached to the end of the inner tubing 74 and the valve seat member 78a. The cap member 78e includes a seal 78g to form a fluid seal in a cap member recess 80c (FIG. 5) within the plunger body 80a during normal operations of filling (FIG. 4) and discharging (FIG. 6) of the syringe 20. The compression spring 76 behind the compression handle 58 maintains tension on the inner tubing 74 within the syringe 20 to aid in maintaining the seal between the inner plunger assembly 78 and the outer plunger assembly 80.

As shown in FIG. 4, the barrel 52 includes an end portion 52a, of reduced diameter, adapted to receive an insert, e.g., of stainless steel. The insert has a bore 86a therethrough. The bore 86a includes a threaded bore portion 86b for receiving a needle mounting insert 88 and a medial bore portion 86c which terminates at a tapered bore portion 86d formed by a seat 86e. The needle mounting insert 88 includes a bore 88a (FIG. 6) extending therethrough. A spring 90, positioned between a needle mounting insert face 88b and a seal plug 92, provides a slight force against the seal plug 92 to form a seal with the insert seat 86e. The needle mounting insert 88 includes an outer end 88c adapted to receive a needle 89.

With reference to FIG. 4, during normal filling operations, the fluid is forced through the inner tubing 74 and against the valve body 78c causing compression of the spring 78d and unseating the valve body 78c from the seat 78b. As the fluid flows past the inner plug assembly 78 it begins to fill the forward end of the barrel 52 causing the plunger assembly 70 to slide rearwardly. It is important to understand that during the filling process, the insert spring 90 maintains a force such that the seal plug 92 remains seated against the insert seat 86e. It may be desirable to accommodate the force required to slide the plunger assembly 70 during the filling of the barrel 52. This can be provided by a tension force in the spring 66 exerting a force on the compression handle 58 which in turn is transferred to the shaft 60 attached to the outer plunger assembly.

Figure 6:
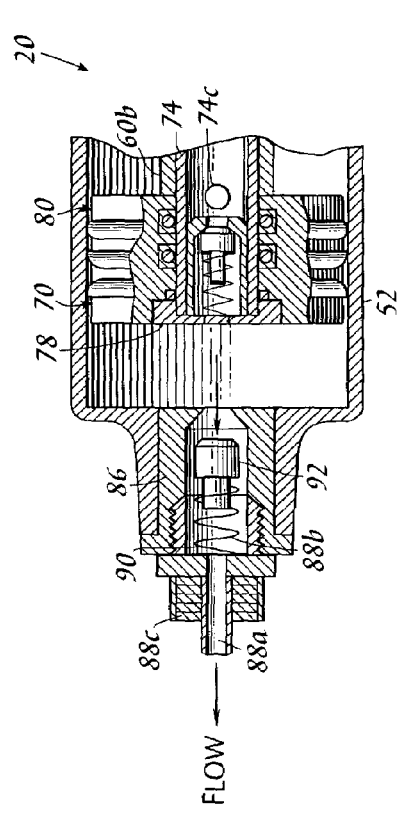
FIG. 6 is a partial side elevational view of a portion of the syringe of FIG. 4 shown in the discharge process.

As shown in FIG. 6, after the filling operation has been completed, the valve body 78c is again seated with the seat 78b. As the operator squeezes the compression handle 58 toward the stationary handle 56, the plunger assembly 70 is forced forwardly and the force of the spring 90 is overcome allowing the seal plug 92 to unseat. This in turn allows the fluid to flow through the needle mounting insert 88 and out through the needle (not shown).

Referring to FIGS. 4 and 5, the forward end 74b of the inner tubing 74 includes one or more side openings 74c which are used in retrieving fluid from the syringe 20. As shown in FIG. 5, to retrieve fluid from the barrel 52 of the syringe 20, the inner tubing 74 is manually forced forward, compressing the compression spring 76 behind the compression handle 58, thus allowing the fluid to flow through the side openings into the inner tubing 74 and back into the reservoir 22 via the pump 18 and connecting tubes 24 and 42.

Referring to FIG. 1, the unit pump 18 may be controlled by the computer 16 in the form of a microchip connected to a livestock handling facility central computer 28, a photoelectric cell, manual three-way (reverse, off, start) selector switches, push buttons, and the dose syringe 20. Of course the buttons and switches, for example, can be exchanged for touch screen controls. The system 10 allows the animal to be weighed, calculates an accurate dosage of a given fluid, and delivers the proper dosage to the dosage syringe 20.

Although not shown in FIG. 1, the dosage system 10 may be equipped with an automatic sensing device for monitoring the level of the medicine in each unit reservoir 22 at all times to ensure that there is enough fluid in the specific reservoir 22 to fill the syringe 20 with an adequate amount of fluid for the dosage. As discussed above, the syringe 20 will also permit the contents of the syringe 20 to be returned to the reservoir 22 via the first and second connecting tubes 24 and 42, respectively, in the event the syringe 20 has been inadvertently or accidentally filled.

Figure 7:
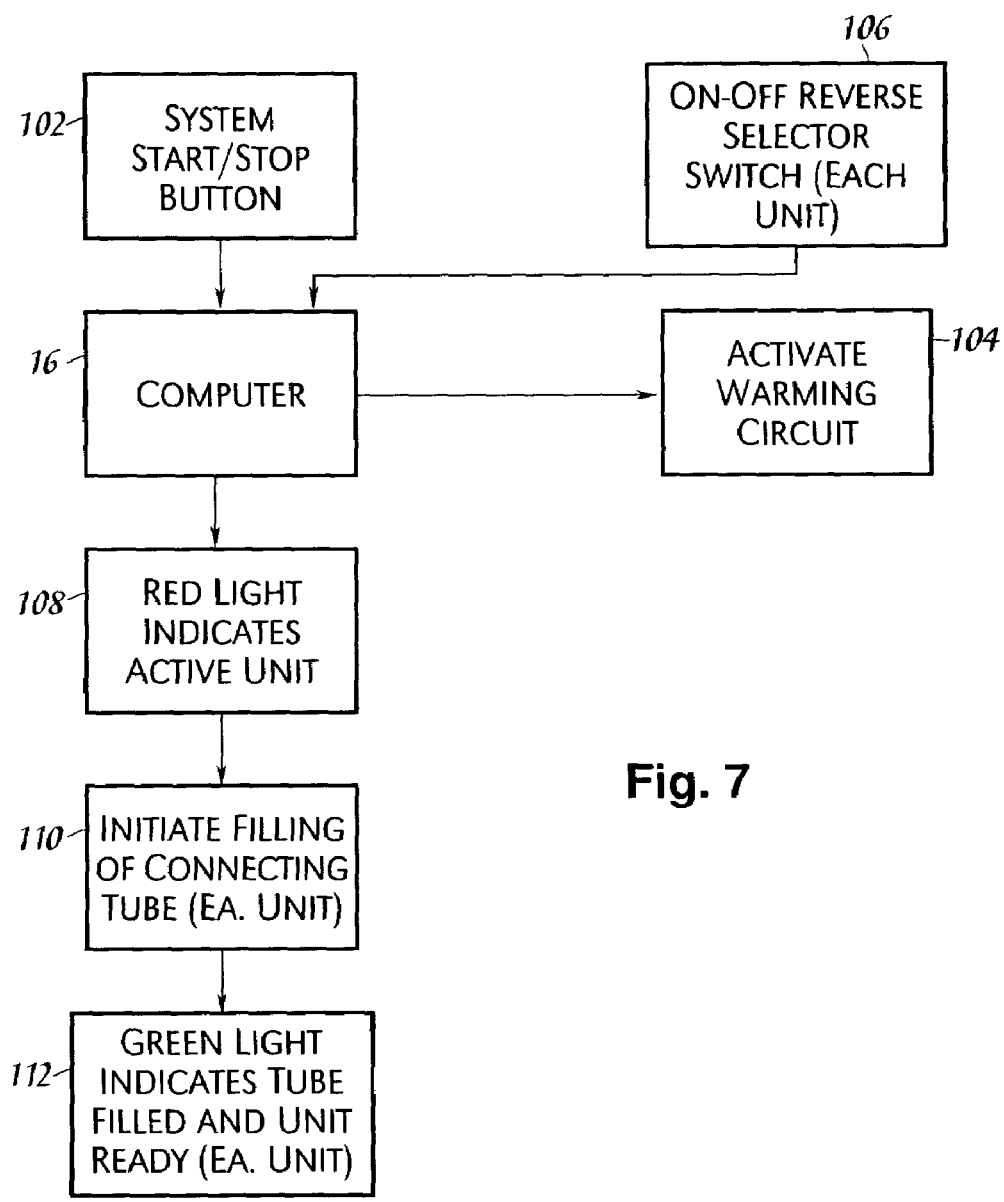
FIGS. 7–9 are schematic block diagrams of the sequential steps of the weight dependent, automatic filling dosage system and method according to an embodiment of the present invention.

The operation and method of use of the dosage system 10 according to the present invention will now be described in detail. It is to be understood that the following steps are only illustrative and one or more of the steps may be modified or omitted without departing from the scope of the present invention. Referring to FIG. 7, the dosage system 10, connected to a 120 volt, 60 cycle alternating current source, is activated by pushing a system start button 102. Simultaneously or separately if desired, a warming circuit 104 may be energized. The warming circuit 104 allows heat-tracing wires to heat each unit 15 in an apparatus housing the plurality of unit reservoirs 22 and also the connecting tubes 24 and 42 between the reservoirs 22 and the syringes 20 when the temperature falls to (or below) a predetermined level. This feature may be necessary or desirable to protect the dosage system 10, the stability of the substance(s), medicines(s) or chemical(s), or to insure their ability to flow from the reservoirs 22 to the syringe 20 at low temperatures. It is anticipated that the dosage system 10 may be used in environments that are not protected from the natural weather conditions. As such, it is extremely important for the dosage system 10 of the present invention to be dependable, usable and accurate in a wide variety of climatic conditions.

Initially, all substances or medications that are known or desired for use on a group of subjects or animals are determined and each unit reservoir 22 is filled with the designated medicine or chemical. Referring to FIG. 2, a fluid container 32 of chemical is attached to the dosage system 10 by turning it upside down, inserting it into the container receptacle 30 and penetrating the plug 36 of the fluid container 32 with the pointed end 34d of the draught and vent spikes 34b as shown in FIG. 2. This allows fluid to flow from the sterile drug container 32 through the draught spike 34b into the reservoir 22 via the filler hose 40. Air is allowed into the fluid container 32 as the fluid exits via the vent spike 34b and the air vent hose 38. The two-way stopcock valve 44 between the reservoir 22 and the pump 18 is turned to the open or "on" position.

The computer 16 is programmed, either manually or otherwise, for each of the medications in each unit 15. For example, the computer 16 may be programmed to calculate a medication dose in unit #1 at the rate of two cubic centimeters per hundred weight (2 cc/100#) and the medication in unit #2 may be administered at the rate of three cubic centimeters per hundred weight (3 cc/100#).

Referring to FIG. 7, each individual unit 15 containing fluid that is known or desired to be administered to a group of animals is activated by manually turning a selector switch 106 to the "on" position. A red light 108 signals each unit which is active and initiates the step 110 of filling with fluid the connecting tubes 24 and 42 from the reservoir 22 to the syringe 20. Once the first connecting tube 24 has been filled, a green light 112 is lit signifying the first connecting tube 24 is full and the unit 15 is ready for the syringe 20 to be filled. This step 110 is necessary to purge air from the system and ready the syringe 20 for filling with the proper amount of antibiotic/chemical fluid.

Figure 8:
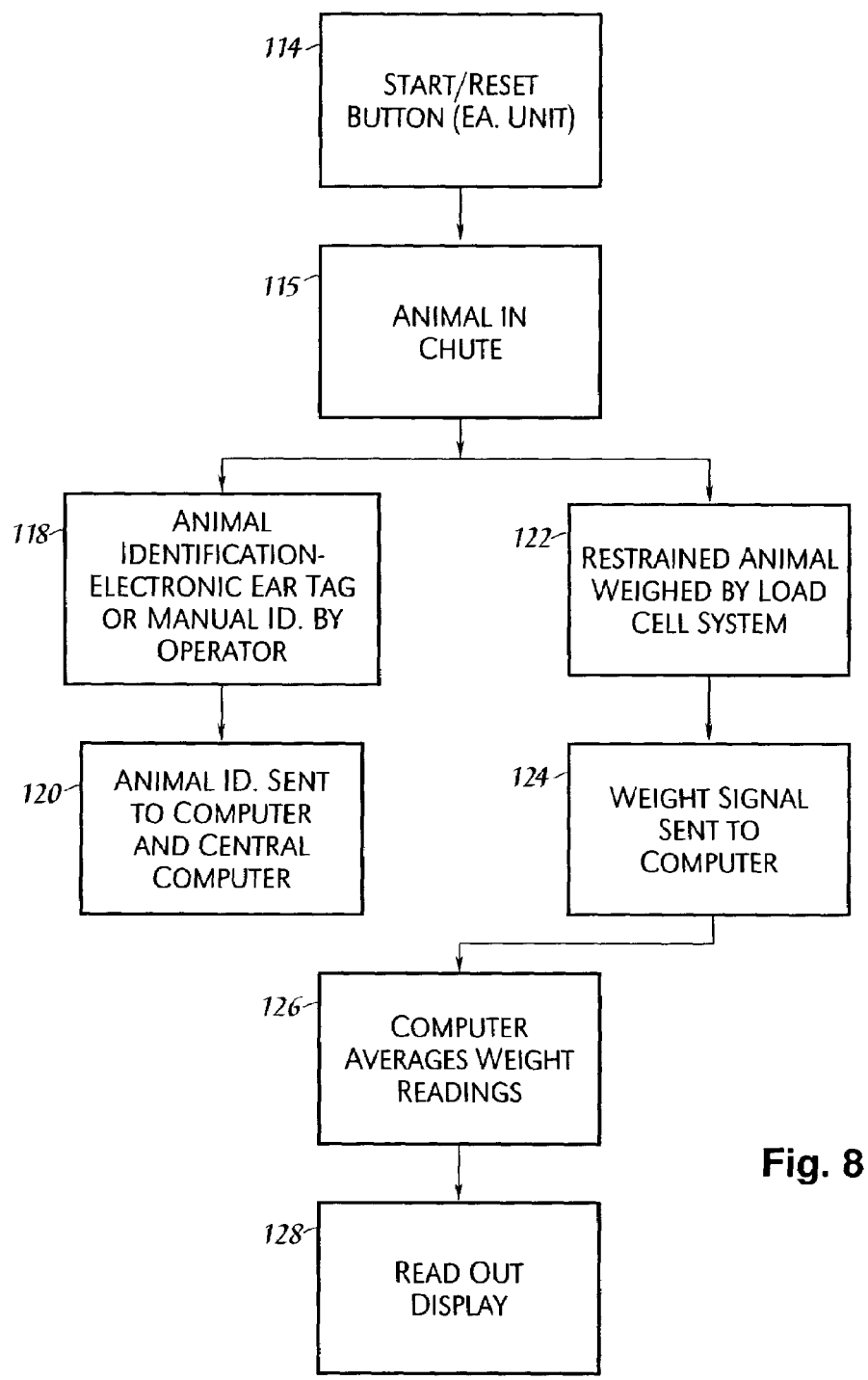

Referring to FIG. 8, a start/reset button 114 at each readied, active unit 15 is then pushed making the active units 15 ready to fill the respective syringes 20. If additional units 15 are required at any time, the selector switches 106 (FIG. 7) controlling those units 15 are turned to the "on" position and those units 15 are activated. With the appropriate units 15 activated, the system 10 is ready. Referring to FIG. 8, an animal enters the restraining squeeze chute 12 (FIG. 1) and is restrained in step 115. The animal is identified 118, e.g., by an ear tag read by a scanner or manually by the operator. The animal identification is transmitted 120 to the computer 16 and the central computer 28. State of the art technology allows electronic identification (ID) tags to accomplish identification. Thus, if the livestock facility utilizes electronic ear tags, a signal is sent on to the central computer 28 which identifies the animal. Alternatively, identification may be manually done by the operator inputting the animal identification on a keyboard attached to the computer 16.

Upon the animal being restrained in the squeeze chute 12, it is weighed 122 by the load cell system 14 (FIG. 1). The load cell system 14 sends a digital or analog signal 124 to the computer 16 recording the weight of the animal. This expression of weight may be in the form of a RS232 or RS485 computer function. An averaging circuit is built into the computer 16 in case the load cell system 14 does not come up with an accurate instant weight for the animal. In step 126, the animal's weight is calculated by averaging the high and low weight readings sensed by the load cell 14 when the animal is secured in the chute 12. It is to be understood that such load cell technology is readily available commercially from various manufacturers, including Tru-Test, COTI Inc., and Incell, to name but a few. The load cell system 14 also includes a read-out display 128 of the animal's weight as indicated in FIG. 8.

If there is a previously determined health program established in the central computer 28, the complete health, treatment, and medical history of the animal in the squeeze chute 12 will be reviewed and next treatment options will be sent to the computer 16 and the proper unit(s) 15 will be activated. Should there be an on-premise main computer 28 to perform this function, a pilot light will be lit signaling the operator to load the station with the proper medication and turn the selector switch to the "on" position, thus filling the connecting tube between the connecting tubes 24 and 42 between the fluid reservoir 22 and the syringe 20.

Figure 9:
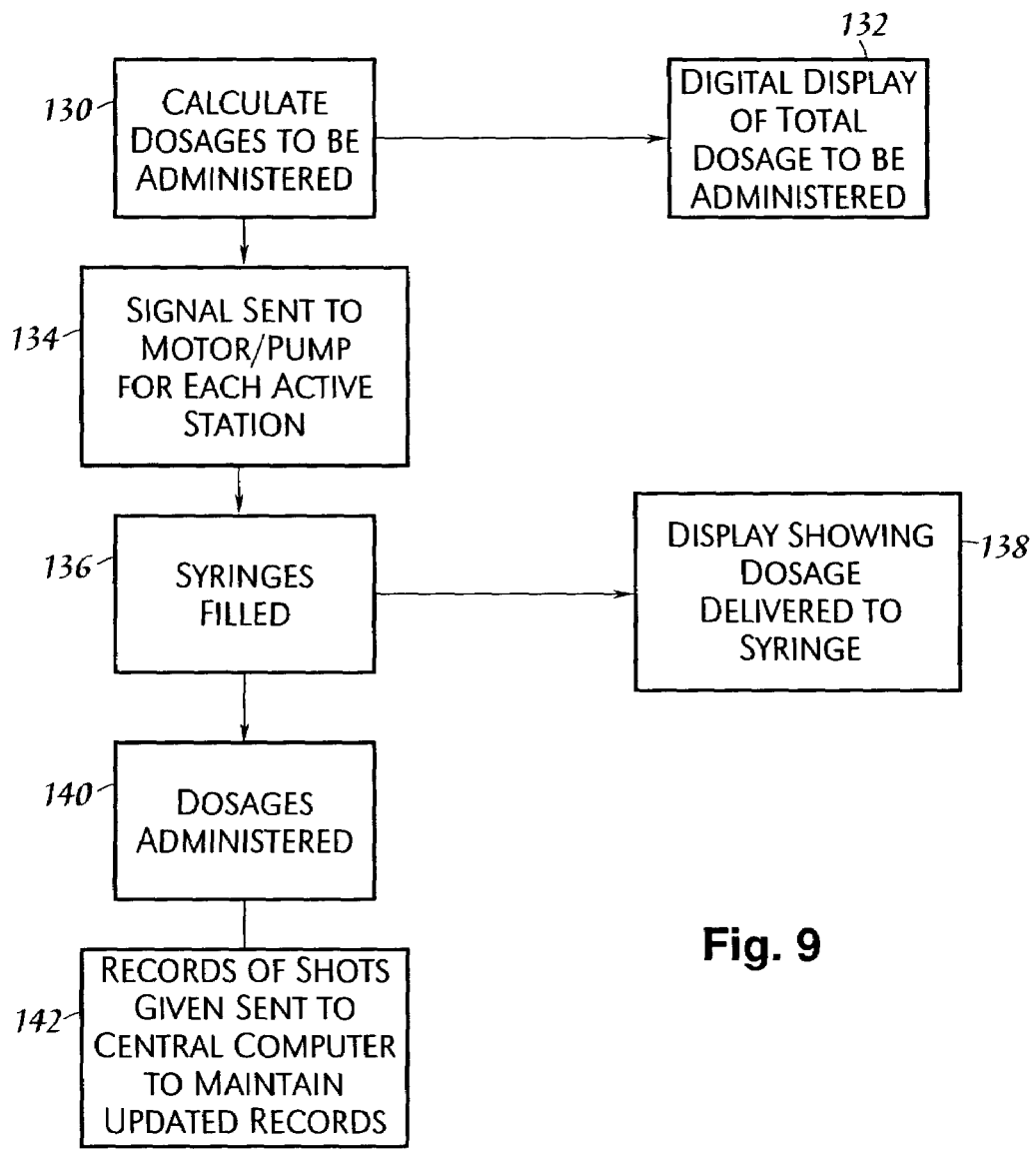

Regardless of whether the units 15 are activated manually or computer-controlled, in step 130 shown in FIG. 9, the computer 16 receives the load cell input and calculates the proper doses of the substances for the animal according to its weight. This is accomplished by multiplying the weight of the animal by the dosage per 100 pounds. This assures that a proper amount of fluid will be accurately delivered to the syringe 20. In effect, it simply calculates the dosages of fluids to be administered. The total dose to be administered may be displayed 132 on a read-out display, e.g., a digital read-out display.

The computer 16 sends a signal 134 to the pumps 18 of each active station to simultaneously fill the required syringes 20 according to the weight of the animal to be treated. In the preferred embodiment of the present invention, the computer 16 interfaces with a control motor of the pump 18. In the preferred embodiment, the computer 16 interfaces with the motor of the FMI pump 18 regarding the number of piston revolutions it must turn as each rotation of the FMI pump piston at a pre-calculated angle of deviation from 180 degrees delivers a predetermined accurate amount of fluid to the dose syringe 20.

The syringes 20 are automatically filled 136 with the proper averaged dosages. Once the syringe 20 has been filled, a digital display 138 will be lit showing the exact dosage which has been delivered to the syringe 20. This signal will be generated when the computer 16 calculates the dosage to be administered. The dosages are administered 140 to the animal. No more than 10 cc of fluid may be administered at any one injection site in order to prevent tissue residue. To accomplish this it is necessary that the dosage calculated be divided into 10 cc maximum or equal aliquots. For example, if the dosage to be administered by the chute operator is 24 cc, the syringe 20 would first be filled with 8 cc. As the pistol grip handle of the syringe 20 is depressed, the fluid is administered and the syringe 20 is emptied. Upon the syringe 20 being emptied, a signal is sent to the computer 16 that the syringe 20 is empty. For example, a switch closes upon the syringe 20 being emptied and sends a signal to the computer 16. When the operator releases the handle, the switch will then tell the computer 16 to fill the syringe 20 with the second 8 cc dosage. The above procedure will then be repeated. Next the computer 16 will signal the pump 18 to provide the remaining 8 cc to the syringe 20. Upon the animal being given the required shots, the animal is released from the squeeze chute 12 and the read-out from the load cell 14 returns to "0" weight balance.

The treatment administered to the animal may be automatically recorded 142 on the central computer 28 to maintain current medical records on each of the animals. This can be done by outfitting the weight dependent automatic dosing system 10 with a sending device to forward the weight of the animal, drug or chemical selected, and the amount used, to the on-premise central computer 28. There it would be recorded as a part of the individual record of that animal. This step would effortlessly document events affecting slaughter times, total treatment costs, to-date treatment costs, etc.

Alternatively, the medicine or chemical dosage for any animal that is calculated by the computer 16 could be automatically recorded on a memory device of a chute side computer whereby it could be later permanently documented. Either way it is an automatic documentation step that would assure accuracy of health records, thereby saving time and money.

Referring to FIG. 1, a photo-electric eye circuit for each active unit 15 may monitor the fluid level in each reservoir 22. When the reservoir 22 is empty or nearly empty, the photo-electric eye circuit shuts down the pump 18 and remembers the amount of fluid that has been delivered to the syringe 20. Once a fresh bottle 32 of fluid is put in the unit 15, the operator pushes the start button 114 to reactivate the unit 15. At that point, the balance of the dose fluid is delivered to the syringe 20.

Referring to the embodiment in FIGS. 1–9, at the end of a work cycle, the only drug or chemical left in the system should be confined to the reservoir 22 and the connecting tubes 24 and 42. There should be no fluid in the syringe 20, but if there is, the following procedure will allow its return to the reservoir 22 via the connecting tubes 24 and 42. The unused portion of the fluid is returned to the reservoir 22 in the following manner. The "on-off-reverse" selector switch 106 is turned to the "reverse" position which reverses the direction the pump 18 pumps fluids. The "start" button 114 is pushed. The inner plunger assembly 78 of the plunger assembly 70 of the syringe 20 is slid forwardly of the outer plunger assembly 80 to allow reverse movement of fluid in the syringe 20, if any fluid remains therein. The ball and spring check valve 24a located at the junction of the first connecting tube 24 and the dosing syringe 20 is activated to allow air to enter the system and displace the fluid as it is returned back to the reservoir 22. This allows the reversed pump 18 to return the uncontaminated, unused portion of the fluid from the dose syringe 20 and first connecting tube 24 back into the reservoir 22, thus, minimizing waste. Note the air filter 24b atop the ball and spring check valve 24a assures cleanliness of air as it enters the closed system. When all of the fluid has returned to the reservoir 22, the "on-off-reverse" selector switch 106 is turned to the off position. The stopcock valve 44 between the reservoir 22 and the fluid metering pump 18 is turned to the off position.

The system is flushed with distilled water until clean and left loaded with fresh distilled water to keep it moist in order to prevent deterioration of the working parts of the pump 18.

The unit 15 can be left on to keep the warming circuit 104 active for the protection of the working parts of the system and liquids at low ambient temperatures or it can be shut down by pushing the stop button 102.

The cleaning and disinfecting of the internal pump 18, connecting tubes 24 and 42, and the dosing syringe 20 can be accomplished in the following manner. The stopcock valve 44 between the fluid reservoir 22 and the flush port 50 is turned to the "off" position. The stopcock valve 46 between the pump 18 and the flush port stopcock valve 48 is turned to the "flush" position. This connects clean sterile flushing fluid to the pump 18, connecting tubes 24 and 42, and dosing syringe 20. The "on-off-reverse" selector switch 106 is turned to the "on" position and the start button is pushed. The connecting tubes 24 and 42 and dosing syringe 20 are filled with clean sterile flushing fluid. The syringe 20 is emptied. The steps of filling and emptying the syringe 20 are repeated until an adequate amount of the flushing fluid has been pumped through the system to thoroughly clean it. Chemical disinfectant may be added to the flushing fluid but it must be followed by repeated flushings of pure, clean flushing fluid in order to remove any chemical residue from the system.

After the system has been adequately flushed, the "on-off-reverse" selector switch 106 is turned to the "off" position. The 2-way stopcock valve 48 between the pump 18 and the flush media reservoir (not shown) is turned to the "off" position. This fluid will remain in the system until just prior to the beginning of the next work cycle, when it will be flushed, freeing the connecting tubes 24 and 42 and syringe 20 to be filled with drugs (or chemicals). This not only lubricates the pump 18, it also enhances pump priming at the beginning of the next work cycle and protects the inner working parts of the pump 18. The 2-way stopcock valve 44 between the pump 18 should remain in the "off" position until the next work cycle.

The procedure for cleaning and disinfecting the fluid reservoir 22, pump 18, connecting tubes 24 and 42, and dose syringe 20 is basically the same as described above except flush solution is substituted for the drug or chemical via the draught/vent spike 34b. The system is activated. The flush port stopcock valve 48 is in the "off" position and the two-way stopcock valve 44 between the fluid reservoir 22 and the pump 18 is turned to the "on" position. The connecting tubes 24, 42 and the syringe 20 are filled with flush fluid. The syringe 20 is emptied. This is repeated until the fluid reservoir 22, connecting tubes 24, 42, and syringe 20 are clean. After the system is flushed, the "on-off-reverse" selector switch 106 is turned to the "off" position.

The system 10 includes one or more of the following additional features. In order to prevent possible mixing of flush solution with the chemical or drug being used in the system, a one-way flush valve 46 is installed in the flush port 50 at the junction with the second connecting tube 42 which connects the fluid reservoir 22 to the pump 18. Although not shown, an air inlet may be inserted in the line between the flush valve 46 and the flush port stopcock valve 48 to allow air into the connecting tubes and the flush solution is discharged from the system through the syringe. The flush valve 46 also serves to prevent backflow of chemical or drug into the flushing system, thus preventing contamination.

An additional desirable feature is an override circuit to override the photo-electric eye circuit which causes automatic shutdown when the fluid level indicates fluid depletion in the bottle. At the end of a work cycle, when it is desirable to flush the system in its entirety, or when a biodegradable antibiotic needs to be removed from the system, it will be necessary to be able to inhibit the circuit which shuts down the pump. This is accomplished by a manually operated "override" circuit which allows the pump 18 to continue to operate until the entire apparatus has been emptied of its contents, thus freeing it up for another operation of flushing.

In case of accidental activation of the partial flush system, a "cancel" switch will be incorporated into the circuit so that flushing fluid cannot be accidentally mixed with the chemical or antibiotic being used at the time.

Thus, it is to be understood that the apparatus and method of the present invention adapted for use in medicating livestock allows, through a series of simple steps, the exact dosage of an antibiotic or parasiticide to be calculated, drawn up automatically in a dosing syringe 20, and then administered to the animal. This can be facilitated with the integration of an electronic load cell device 14 for weighing the animal built into the squeeze chute 12, a computer 16 to receive and interpret the information (weight) from the load cell 14 and send a signal to a metering pump 18 to pump the exact amount of medication into a directly connected syringe 20 for the correct dosage for the animal. Thus, each animal is concisely treated for its exact weight which results in a significant economic impact in the cattle feeding industry due to fewer retreats and the avoidance of chemical and antibiotic wastage.

Figure 10:
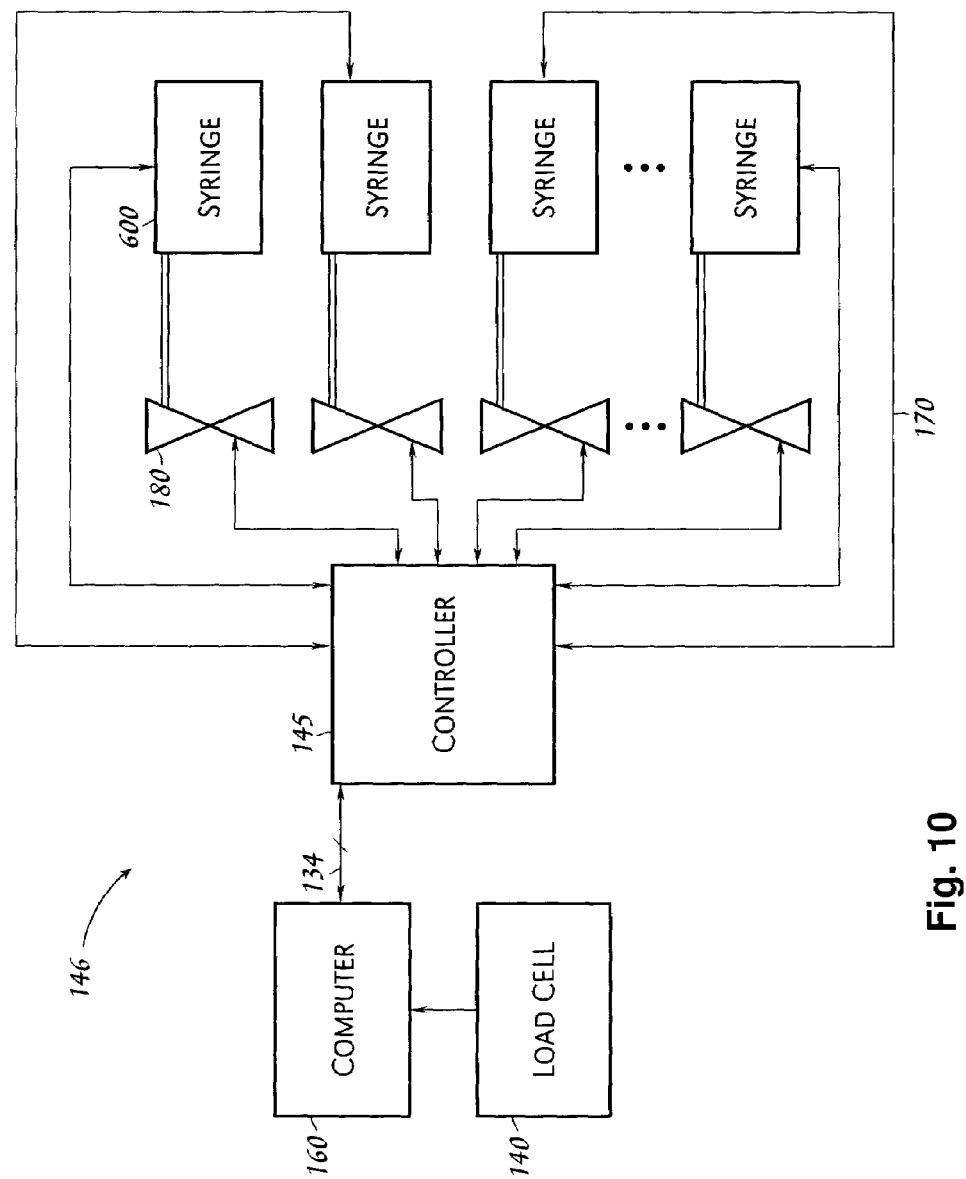
FIG. 10 is a schematic block diagram of the circuit used to control an automatic filling dosage system in accordance with an embodiment of the present invention.

FIGS. 10 and 15 show an alternative embodiment of the present invention. It should be noted that syringe 600 could be used in the embodiment described above with respect to FIG. 1, or any other system for applying medicament to a subject, and is thus not limited to the systems described herein. Alternatively, the syringe 20 could be used in system 146. The syringe 600 differs from the syringe 20, as previously depicted in FIGS. 4–6 and earlier in this specification, in several ways. The syringe 600 allows precise filling using a, for example only, spool valve assembly 610. The valve 610 allows medicament to enter the syringe from the pump 180. The medicament flows from the valve 610 into the barrel 670. By manually actuating the handle assembly 630, and consequently the plunger assembly 620, the medicament is propelled from the barrel 670 through the valve 610 and out of the syringe 600. The single valve 610 takes the place of multiple valves in that it helps control the flow of medicament both into and out of the syringe 600. Reducing the number of required valves helps reduce the number of components that must be maintained throughout the life of the syringe 600. Also, the spool valve 610 may be free of gaskets or elastomers, thereby performing better under pressure and further reducing maintance of the syringe 600. Any well-known spool valve could be used.

Again referring to FIG. 15, the syringe 600 further incorporates a hall-position sensor 640 and LED 650. As will be described more fully in FIG. 11, the sensor 640 works in conjunction with a magnet 660 to determine the medicament volume within the barrel 670 as dictated by the position of the plunger assembly 620. After the desired level of medicament has been sent from the pump 180 into the barrel 670, the computer 160 sends a signal to the LED 650 causing the LED 650 to illuminate. This alerts the user that the system 146 is ready and that the medicament may be administered to the animal at any time. Once the handle assembly 630 has been fully actuated, thus moving the plunger assembly 620 into a closed position, the hall-position sensor sends a signal to the computer 160 indicating the medicament has been administered and that the syringe 600 may again be filled with medicament. The aforementioned signals involving the LED 650 and sensor 660 may be transmitted to the computer 160 via the electrical cable assembly 680. A flexible, stainless steel strength member helps diminish detrimental forces that act upon the electrical cable assembly 680. An example of pump 180 is the SCST-01 Step Motor manufactured by Fluid Metering, Inc. ("FMI") of Syosset, N.Y.

Figure 16A:
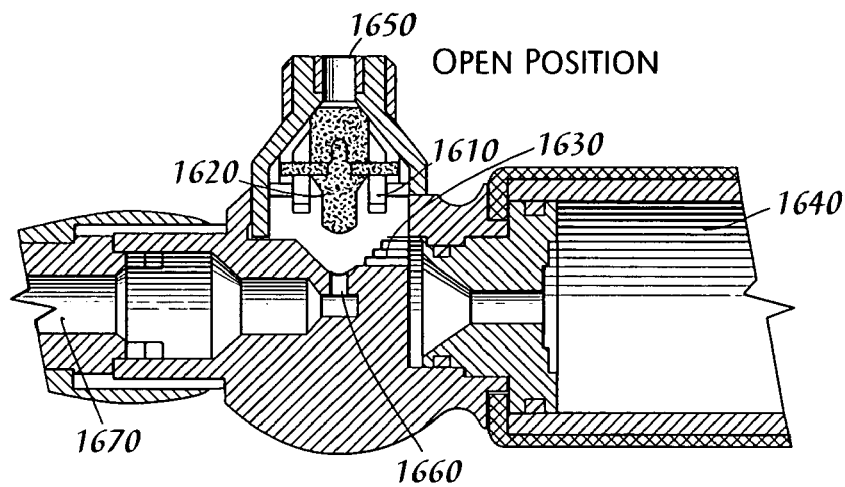
FIGS. 16A and 16B are partial side elevational views of a portion of the syringe of FIG. 15.
Figure 16B:
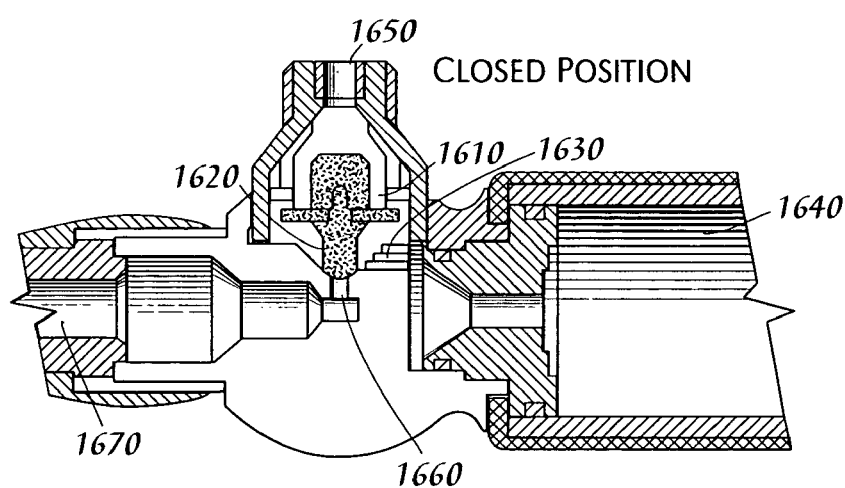

FIGS. 16A and 16B address the valve 610 portion of the syringe 600. As shown in FIG. 16A, the piston 1620 is in the open position in its resting state. When it receives fluid, under pressure, through in-flow port 1650, the piston 1620 moves downward and compresses the piston spring 1610. Doing so allows the incoming fluid to pass through milled ports 1630 into the syringe cylinder 1640. (FIG. 16B.) Once the in-flow of fluid has stopped, the piston spring 1610 returns the piston 1620 to the open position. In the open position the cylinder body is ported 1660 to allow fluid to be pressure delivered from the chamber 1640 through the port 1660 and to the out-flow port 1670.

Figure 11:
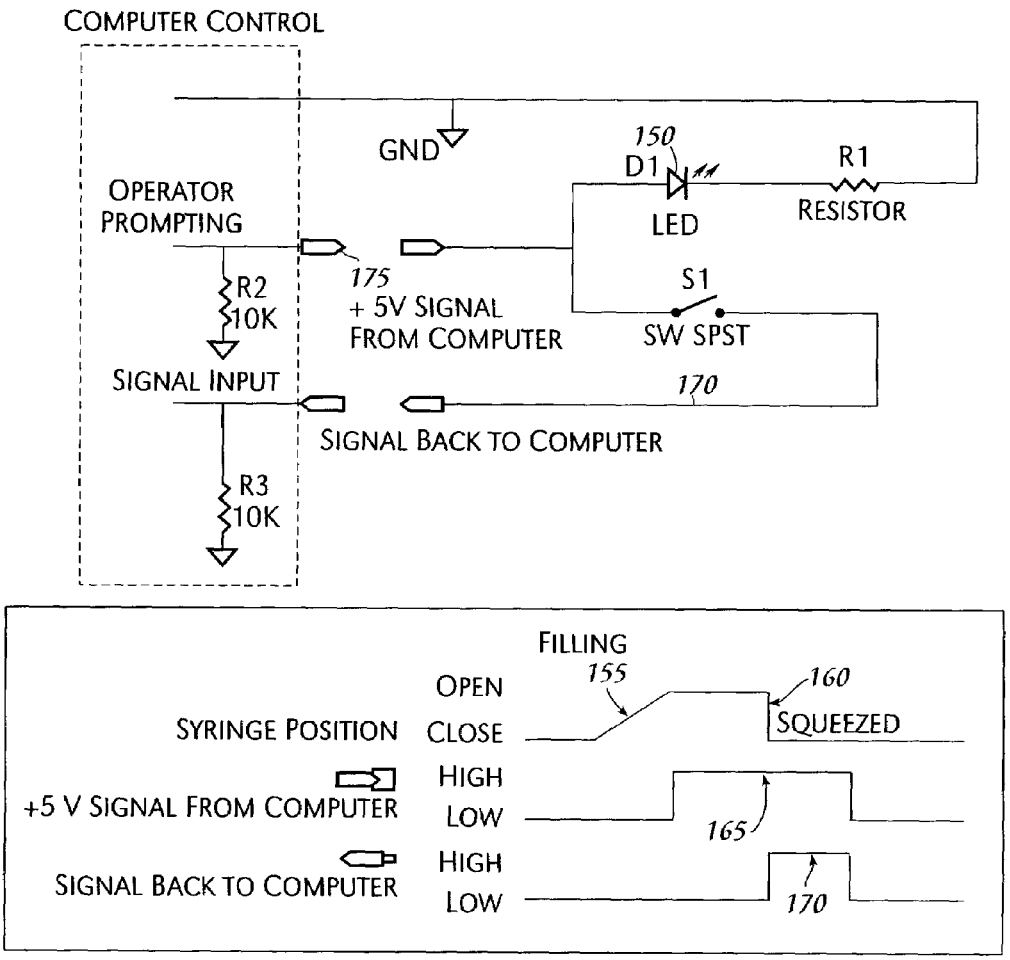
FIG. 11 is a timing diagram used to alert the user to the filling status of the automatic filling dosage system of FIG. 10.

Referring to FIGS. 10–11, the timing aspect of an embodiment of the invention is addressed. The computer 160 sends a signal 134 to the controller 145 and then to the pump 180 of each active station to simultaneously fill the required syringe 600 according to the weight of the animal to be treated. Computer 160 sends the signal 134 to the pumps 180 over a parallel circuit configuration 146. The computer i 60 interfaces with a control motor of the pump 180.

The syringes 600 are automatically filled 136 with the proper dosages. Once the syringe 600 has been filled, the computer 160 will also transmit a +5V signal 175 that activates 165 a LED 150 to indicate the syringe 600 has completed its filling stage 155. The digital display signal 138 will be generated when the computer 160 calculates the dosage to be administered. The dosages are then administered to the animal. The administration of the dose causes the syringe 600 to enter a closed stage 160 whereby a termination signal 170 is transmitted to the controller 145 to indicate the syringe 20 may again be refilled. This also causes the LED 150 to no longer be illuminated indicating to the user that the unit 15 is no longer ready to administer a dose to the animal.

Referring to FIG. 11, as the pistol grip handle of the syringe 600 is depressed, the fluid is administered and the syringe 600 is emptied. Upon the syringe 600 being emptied, a signal 170 is sent to the computer 160 that the syringe 600 is empty. For example, the sensor 640 emits a signal to the computer 160 upon the syringe 600 being emptied. When the operator releases the handle, the sensor 640 will then tell the computer 160 to fill the syringe 600 again. The above procedure will then be repeated. Next the computer 160 will signal the pump 180 to provide the next dose to the syringe 20. This embodiment may incorporate some or all of the features described above with respect to FIGS. 1–9 for implementation in computer 160 and controller 145.

Figure 12:
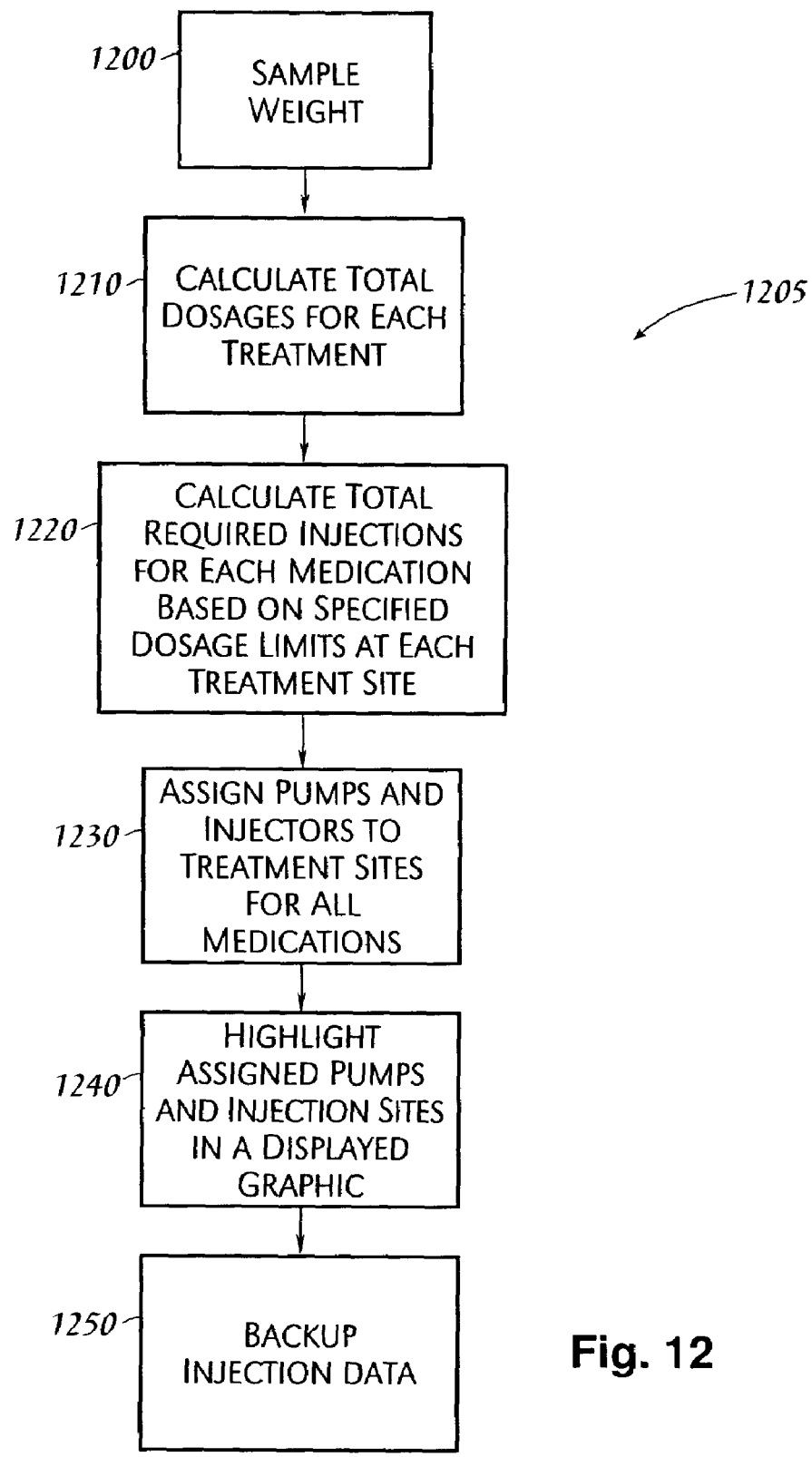
FIGS. 12–13 are flow diagrams of the weight dependent, automatic filling dosage system of FIG. 10.
Figure 13:
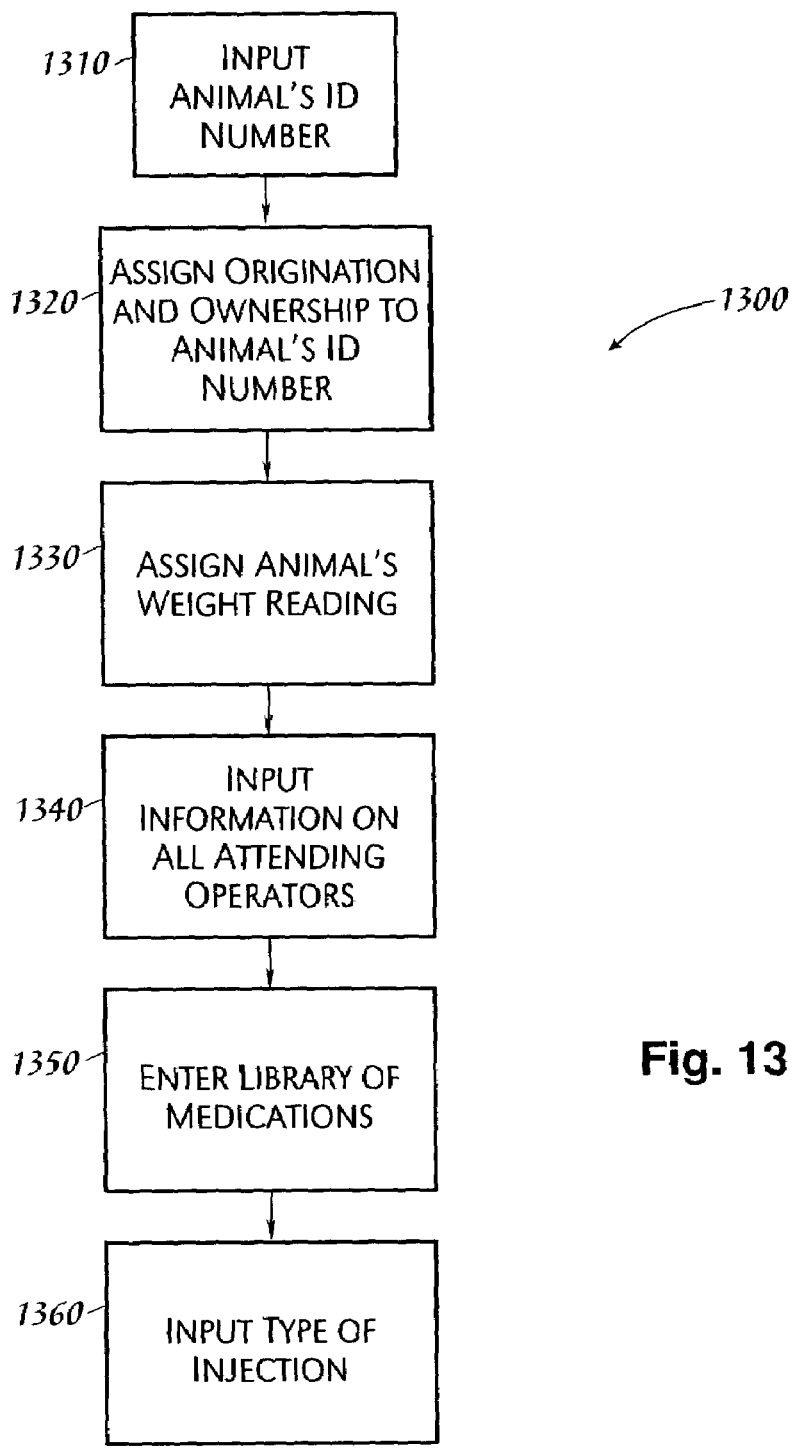
Figure 14:
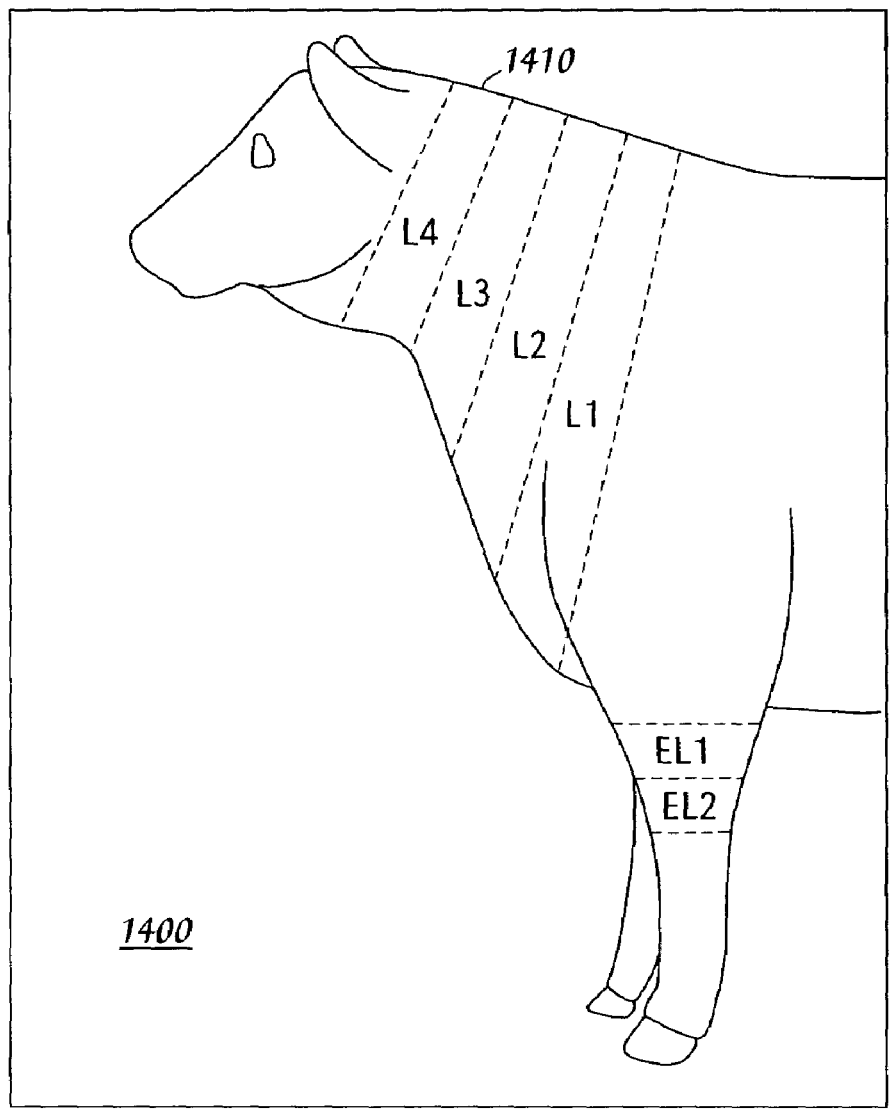
FIG. 14 is a diagram of injection quadrants on a cow or bull, which graphic can be displayed on the system of FIG. 10.

An embodiment of software that can be used to administer and record dosage information is found in FIGS. 12–14. Referring to FIGS. 12 and 14, the animal's weight is sampled 1200. The total dosage for each selected treatment medication is then calculated based on the animal weight data 1210. The software 1205 then calculates the total required injections for each medication based on 10 cc dosage limits 1220 at each quadrant treatment site 1410. For dosages exceeding the 10 cc limit, the software 1205 calculates the average dosage amount required for multiple dosages. The software 1205 then assigns pumps 180 and syringes 600 to treatment sites 1410 for all medications 1230. The software 1205 next highlights the assigned pumps and their related quadrant treatment sites 1410 in a displayed graphic 1240 such as shown in FIG. 14. Finally, at completion of administering the dosage to the animal, the software 1205 will back up the injection data 1250. Thus, the software can assign exact dosages to each pump 180 and associated syringe 600, including which medicines go to which syringe, and then the operator can view the displayed graphic 1400 to determine which syringe 600 to administer to which site 1410.

Referring to FIG. 13, another embodiment of software allows for the tracking of an animal's medical treatment history. This addresses the mounting movement among consumers to know exactly what medications are used in the meat products that they consume. First, the animal's identification number can be input manually by the treatment operator or by the use of a bar code reader that is tied to the treatment computer 1310. The origination and ownership of the animal will be assigned to that animal's number or bar code number 1320. The animal's weight will be determined by the use of a load cell to accurately determine the animal's exact weight for that day's treatment and this measurement can either be manually input or automatically sampled and recorded into the treatment computer 1330. Furthermore, the software 1300 may require the input of attending operators for each treatment procedure 1340. The software 1300 also allows for entry of an unlimited medication library that can be selected by single treatment or a multiple treatment regimen 1350. This library of medications can either be entered manually or by the use of the bar code label on the medication label. The medication library data can indicate, for example, dosage per pound, time period between treatments and the next level of recommended treatment preset by the veterinarian. The tracking of follow up treatments is important in that it will affect the slaughter time of the animal, to date treatment cost and the total treatment costs of each animal. Finally, the software 1300 can keep track of the route of the medicine's administration 1360. Those specifications may include Intramuscular (IM), Subcutaneous (SQ), Intravenous (IV), Pour-on (P/O), Bolus (BO) and Implants. Further, the record will indicate which quadrants 1410 were injected with how much medicament and what type of medicament and by which operator.

Figure 17:
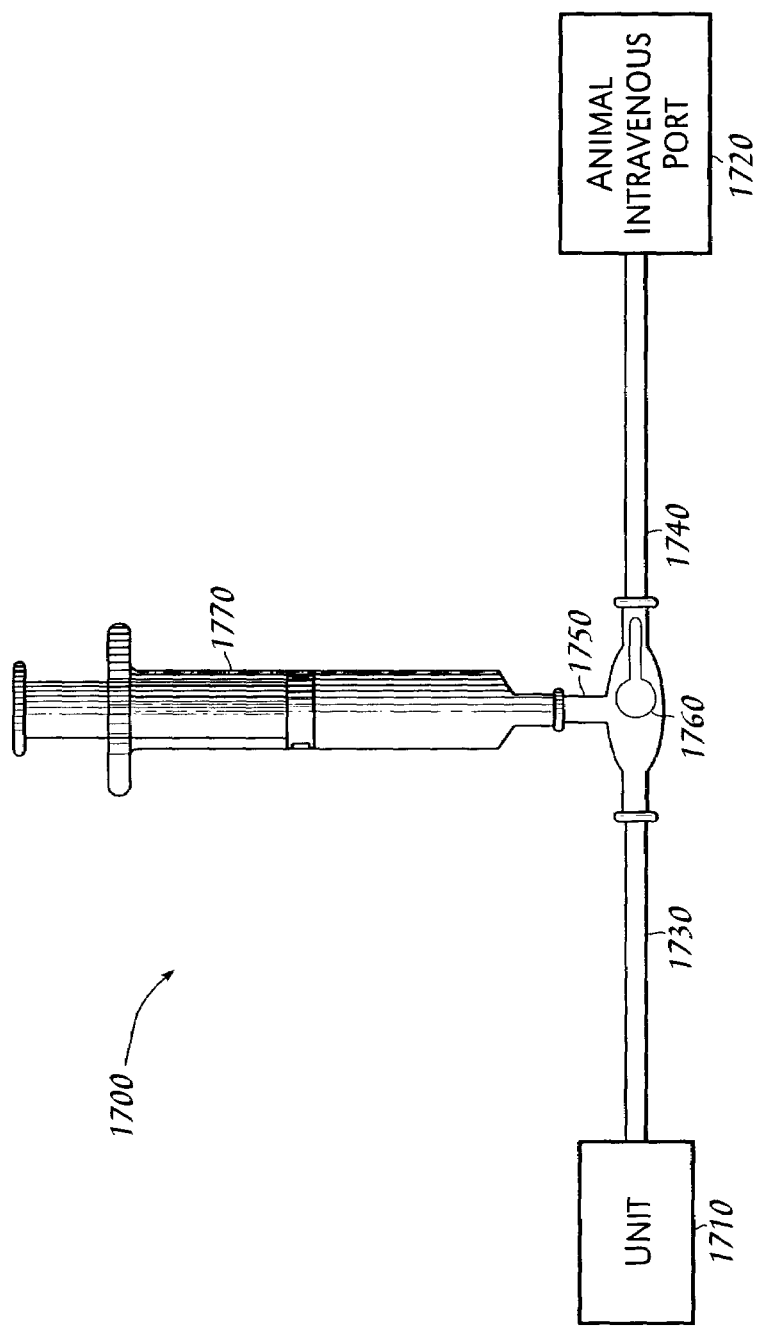
FIG. 17 is a diagram of an embodiment of an intravenous syringe useable in the present invention.

Referring to FIG. 17, another embodiment of the invention allows for intravenous administration of medication. The system 1700 joins the medication unit 1710 to an intravenous port 1720 in the animal. Medication may be administered from the unit 1710, through connection tubing 1730, port 1750, valve 1760, connection tubing 1740 and then into the intravenous port 1720. In addition, medication may be administered from the syringe 1770, through port 1750, valve 1760, connection tubing 1740 and then into the intravenous port 1720. The valve 1760 ensures medication flows from the unit 1710 to the intravenous port 1720 and not into the syringe 1770. The same valve 1760 can be manipulated to ensure medication flows from the syringe 1770 to the intravenous port 1720 and not into the unit 1710. The connection tubing 1730 and 1740, as well as the syringe 1770, may be constructed from transparent materials. This allows the user to monitor medication and blood flow to and from the animal.

It is to be understood that the embodiments of the present invention described above allows a dosage accuracy of 0.5 of 1% for a weight reading within a 20 lb. range.

It is further to be understood that the present invention can also be used with the metric system in addition to the U.S. measurement system. In situations wherein the metric system is utilized instead of the U.S. measures, the dosages will be calculated in kilograms.

The present invention can also provide that each unit be programmable in 0.1 cc increments from 0.5 cc to 10 cc's. This will allow each unit to be programmed to deliver any dosage per 100 pounds desired in 0.1 cc increments from 0.5 cc to 10 cc's. This can be accomplished in one of the two following ways. The software can be programmed so that the desired dosage can be selected electronically or the angle of deviation from vertical of the FMI pump 18 (if preferably used) can be adjusted to change the dosage.

The present invention could also include a web-based data management solution that updates automatically from information collected from the system. Examples of some of the types of information that could be provided are as follows: weight of animal upon arrival at the feedlot; treatment given on arrival; any additional treatment while at the feedlot; and weight of the animal at any time it goes through the chute. This information could be accessed remotely by the owner of the cattle. This would allow the owner to monitor more closely the progress of his animals.

The foregoing disclosure and description of the invention is illustrative and explanatory thereof, and various changes in the size, shape, and materials, as well as in the details of illustrative construction and assembly, may be made without departing from the spirit of the invention.

The invention claimed is:

1. A syringe apparatus comprising:
    a handle assembly,
    a chamber for fluid storage,
    a plunger assembly slidably received in said chamber,
    an in-flow conduit wherein fluid enters a syringe,
    an outflow conduit wherein fluid exits said syringe,
    a valve coupling said chamber, said in-flow conduit and said out-flow conduit,
    wherein said valve is configured to allow fluid to flow from said in-flow conduit to said chamber, and
    wherein said valve is further configured to allow fluid to flow from said chamber to said out-flow conduit, and
    a gun body coupling said handle assembly to said valve, and
    a sensor device coupled to said chamber,
    wherein said sensor device detects fluid level within said chamber.

2. The apparatus of claim 1, wherein said sensor device comprises a magnet coupled to said plunger assembly.

3. The apparatus of claim 1, wherein said sensor device transmits data to a computer.

4. Apparatus for administering fluid comprising;
    a handle assembly,
    a reservoir,
    a plunger assembly slidably received in said reservoir,
    an in-flow conduit,
    an out-flow conduit,
    a valve coupling said reservoir, said in-flow conduit, and said outflow conduit, and
    a gun body coupling said handle assembly and said valve, and
    a sensor device coupled to said plunger,
    wherein said sensor device monitors said position of said plunger assembly.

5. The apparatus of claim 4 further comprising:
    a LED coupled to said gun body wherein said LED indicates said position of said plunger assembly.

6. The apparatus of claim 4, wherein said sensor device comprises a magnet coupled to said plunger assembly.

7. The apparatus of claim 4, wherein said sensor device transmits data to a computer.

* * * * *